(12) United States Patent
Mori et al.

(10) Patent No.: US 9,987,279 B2
(45) Date of Patent: Jun. 5, 2018

(54) PHARMACEUTICAL COMPOSITION FOR PREVENTION AND/OR TREATMENT OF URINARY INCONTINENCE

(71) Applicants: ASTELLAS PHARMA INC., Chuo-ku (JP); CYTOKINETICS INCORPORATED, South San Francisco, CA (US)

(72) Inventors: Shinobu Mori, Tokyo (JP); Yusuke Kajihara, Tokyo (JP); Hiroko Inamura, Tokyo (JP); Takuya Hirata, Tokyo (JP)

(73) Assignees: ASTELLAS PHARMA INC., Chuo-ku (JP); CYTOKINETICS INCORPORATED, South San Francisco, CA (US)

( * ) Notice: Subject to any disclaimer, the term of this patent is extended or adjusted under 35 U.S.C. 154(b) by 0 days. days.

(21) Appl. No.: 15/509,394

(22) PCT Filed: Sep. 9, 2015

(86) PCT No.: PCT/JP2015/075567
§ 371 (c)(1),
(2) Date: Mar. 7, 2017

(87) PCT Pub. No.: WO2016/039367
PCT Pub. Date: Mar. 17, 2016

(65) Prior Publication Data
US 2017/0273979 A1 Sep. 28, 2017

(30) Foreign Application Priority Data
Sep. 9, 2014 (JP) .................... 2014-183434

(51) Int. Cl.
*A61K 31/506* (2006.01)
*A61K 31/40* (2006.01)
*A61K 31/136* (2006.01)
*C07D 401/14* (2006.01)

(52) U.S. Cl.
CPC .......... *A61K 31/506* (2013.01); *A61K 31/136* (2013.01); *A61K 31/40* (2013.01); *C07D 401/14* (2013.01)

(58) Field of Classification Search
CPC ........................ C07D 401/14; A61K 31/506
USPC ........................................ 544/331; 514/275
See application file for complete search history.

(56) References Cited

U.S. PATENT DOCUMENTS

| 2010/0113484 A1 | 5/2010 | Gotanda et al. |
| 2010/0240697 A1 | 9/2010 | Suzuki et al. |
| 2013/0123289 A1 | 5/2013 | Yang et al. |
| 2015/0065525 A1 | 3/2015 | Jasper et al. |
| 2015/0250784 A1 | 9/2015 | Malik et al. |

FOREIGN PATENT DOCUMENTS

| EP | 2 216 021 A1 | 8/2010 |
| JP | 2011-20943 A | 2/2011 |
| JP | 2013-525377 A | 6/2013 |
| WO | 2005/095359 A1 | 10/2005 |
| WO | WO 2011/133888 A1 | 10/2011 |
| WO | WO 2013/151938 A1 | 10/2013 |
| WO | WO 2013/155262 A2 | 10/2013 |

OTHER PUBLICATIONS

Chai et al., Future Directions of Research and Care for Urinary Incontinence, The Journal of Urology, vol. 198, pp. 22-28, 2017.*
International Search Report dated Dec. 22, 2015 in PCT/JP2015/075567 filed Sep. 9, 2015.
Tracy W. Cannon, et al., "Innovations in pharmacotherapy for stress urinary incontinence" Int. Urogynecol. J., vol. 14, 2003, pp. 367-372.
Yasuhiro Kaiho, et al., "Role of noradrenergic pathways in sneeze-induced urethral continence reflex in rats" Am. J. Physiol. Renal. Physiol., vol. 292, Feb. 2007, pp. F639-F646.
N. Klarskov, et al., "Measurement of Urethral Closure Function in Women With Stress Urinary Incontinence" The Journal of Urology, vol. 181, Jun. 2009, pp. 2628-2633.
The Journal of Urology, vol. 179, No. 4, May 20, 2008, pp. 569-570.
Bernhard Schuessler, et al., "Pharmacologic treatment of stress urinary incontinence: expectations for outcome" Urology, vol. 62, Supplement 4A, Oct. 2003, pp. 31-38.
Alan J. Russell, et al., "Activation of fast skeletal muscle troponin as a potential therapeutic approach for treating neuromuscular diseases" Nature Medicine, vol. 18, No. 3, Mar. 2012, 5 pages.
H. D. Schrøder, et al., "Fiber Types in the Striated Urethral and Anal Sphincters" Acta Neuropathologica, vol. 60, 1983, pp. 278-282.
Th. Dimpfl, et al., "Myogenic Changes of the Levator Ani Muscle in Premenopausal Women: The Impact of Vaginal Delivery and Age" Neurourology and Urodynamics, vol. 17, 1998, pp. 197-205.
European Search Report dated Jan. 8, 2018, in European Application No. 15839636.6.
Singapore Office Action dated Jan. 9, 2018, in Singapore Application No. 11201701019U.

* cited by examiner

*Primary Examiner* — Deepak R Rao
(74) *Attorney, Agent, or Firm* — Oblon, McClleland, Maier & Neustadt, L.L.P.

(57) ABSTRACT

The problem to be solved by the present invention is to provide a novel pharmaceutical composition for prevention and/or treatment of urinary incontinence, which differs from conventional drugs. The present invention provides a therapeutic agent for prevention and/or treatment of urinary incontinence having 1-[2-({[trans-3-fluoro-1-(3-fluoropyridin-2-yl)cyclobutyl]methyl}amino)pyrimidin-5-yl]-1H-pyrrole-3-carboxamide or a salt thereof, as an active ingredient.

3 Claims, 2 Drawing Sheets

PHARMACEUTICAL COMPOSITION FOR PREVENTION AND/OR TREATMENT OF URINARY INCONTINENCE

TECHNICAL FIELD

The present invention relates to novel pharmaceutical application of a compound having fast skeletal muscle troponin activation as a pharmaceutical composition for prevention and/or treatment of urinary incontinence.

BACKGROUND ART

"Urinary incontinence" is a condition, perceived objectively, in which urine leaks involuntary, and is both a social and a hygienic problem (J. Clin. Pharm. Ther., 25(4), 251-263 (2000)). Typical types of urinary incontinence are urge urinary incontinence, stress urinary incontinence, and mixed urinary incontinence, which is a mixture of the two types.

The most common type of urinary incontinence is stress urinary incontinence, and about 50% of women who suffer urinary incontinence reportedly have stress urinary incontinence (Int. Urogynecol. J., 11(5), 301-319 (2000)). "Stress urinary incontinence" is a condition in which urine leaks involuntarily, regardless of contraction of the bladder, with elevated abdominal pressure associated with coughing, sneezing, movement, or the like. The causes of stress urinary incontinence are divided mainly between two causes. One cause is bladder neck and urethral hypermobility, in which transmission of abdominal pressure to the urethra is poor due to the bladder neck dropping based on relaxation of the pelvic floor muscle, and when abdominal pressure rises, intravesical pressure rises without increased urethral pressure pressure, causing urine to leak. Another cause is reduced sphincter function due to intrinsic urethral sphincter insufficiency, causing urine to leak with increased abdominal pressure. The onset of stress urinary incontinence is very likely related to embrittlement of the pelvic floor muscle and/or reduced sphincter function due to age or childbirth. In particular, trauma to the pelvis due to pregnancy or vaginal birth is a known risk factor for onset of persistent stress urinary incontinence, and the incidence of stress urinary incontinence within 5 years after first childbirth is reportedly about 30% (Neurourol. Urodyn., 21(1), 2-29 (2002)).

"Urge urinary incontinence" is a condition in which urine leaks involuntarily following a sudden, irresistible strong urge to urinate (urinary urgency). "Mixed urinary incontinence" is a condition in which different types of urinary incontinence occur, and in most cases is a mixture of urge urinary incontinence and stress urinary incontinence.

Urinary incontinence has a major impact on quality of life (QOL). Patients acutely aware of the symptoms of incontinence have a restricted range of activity, and feel socially isolated and lonely.

Drugs reported to have a therapeutic effect on stress urinary incontinence are drugs having a serotonin-norepinephrine reuptake inhibiting effect (SNRI), drugs having a selective norepinephrine reuptake inhibiting effect (NRI), and the like. Sudden increase in abdominal pressure and intravesical pressure found with coughing, sneezing, movement, or the like contracts the external urethral sphincter through spinal reflex, but norepinephrine and serotonin increases excitability of the intraspinal Onuf's nucleus, which is the nucleus of origin of the somatic motor nerve governing the external urethral sphincter. Specifically, SNRI and NRI medications reportedly excite the pudendal nerve comprising the somatic motor nerve and increase contraction of the external urethral sphincter by accelerating excitability of the Onuf's nucleus (Non-patent Documents 1 and 2).

Although the SNRI duloxetine was reportedly effective on stress urinary incontinence in a clinical study, undesirable adverse drug reactions such as suicide attempts were reported. The country where duloxetine is approved as an urinary incontinence therapeutic agent is restricted to only Europe. Although the NRI nisoxetine, in a preclinical study, reportedly increased urethra internal pressure and improved incontinence induced by sneezing (Non-patent Document 2), no clinical study has been carried out for stress urinary incontinence. The NRI (S,S)-reboxetine reportedly increased urethral resistance in a clinical study, and is reportedly effective for stress urinary incontinence (Non-patent Documents 3 and 4), but has not yet been received pharmaceutical marketing approval as a urinary incontinence therapeutic agent.

Drugs having an al-receptor agonist effect contract the urethra through al-receptors present in urethral smooth muscle and have been shown in a clinical study to be effective on stress urinary incontinence, but have not yet received pharmaceutical marketing approval as a stress urinary incontinence therapeutic agent due to cardiovascular adverse drug reactions such as elevated blood pressure (Non-patent Document 5).

As noted earlier, raising urethral resistance to maintain control of urinary incontinence seems to be effective as a drug therapy for stress urinary incontinence, and drugs based on several mechanisms of action have been studied. Due to problems such as adverse drug reactions, however, no urinary incontinence therapeutic agent has been approved globally, and development of a stress urinary incontinence therapeutic agent based on a novel mechanism of action would be greatly desirable.

The external urethral sphincter and the pelvic floor muscle which supports the structures related to the bladder and urethra and the like are types of skeletal muscle. Myofibrils, which are the contractile organ of skeletal muscle, link together units called sarcomeres comprising thin actin filaments and fat actin filaments. Skeletal muscle contracts by an actin filament and a myosin filament interacting repeatedly such that the two filaments slide past each other.

The contractile response of skeletal muscle is caused by release of calcium ions from intracellular sarcoplasmic reticula according to excitation of the somatic motor nerve governing each skeletal muscle. Intracellular calcium ions binding to a troponin complex, which is one component protein of an actin filament, changes the structure of the troponin complex to allow the actin filament to interact with a myosin filament. Thus, the troponin complex functions in the actin filament as a regulator protein mediating a contractile response of the skeletal muscle which is dependant on the concentration of calcium ions.

Skeletal muscles are classified as fast-twitch muscles and slow-twitch muscles, where fast muscles are functionally characterized by a faster contractile rate with greater muscle tension than slow muscles. Troponin complexes combine different isoforms of troponin in fast and slow muscles to form fast- and slow-muscle troponin complexes.

Drugs having fast skeletal muscle troponin activation are known to act on fast-muscle troponin complexes to increase the sensitivity of the troponin complexes to intracellular calcium ions so as to increase the contractile force of fast muscles (Non-patent Document 6).

1-[2-({[Trans-3-fluoro-1-(3-fluoropyridin-2-yl)cyclobutyl]methyl}amino)pyrimidin-5-yl]-1H-pyrrole-3-carboxamide (hereafter also called "compound A") is a compound having fast skeletal muscle troponin activation (Patent Document 1). Compound A has been shown to shift the concentration-response curve of intracellular calcium ions concentration and muscle tension to the left in rat diaphragm myofibrils and rat extensor digitorum longus muscle including a fast-muscle component (Patent Document 2, 3). Compound A also reportedly has actions reinforcing the contractile response of a rat diaphragm induced in vitro by transmural electrical stimulation, and reinforcing extensor digitorum longus muscle contractile response by electrical stimulation of the rat fibular nerve in vivo (Patent Document 2, 3).

The external urethral sphincter and the pelvic floor muscle are skeletal muscles which reportedly include a fast-muscle component (Non-patent Document 7, 8).

PRIOR ART DOCUMENTS

Patent Documents

Patent Document 1: International Patent Application No. WO2011/133888
Patent Document 2: International Patent Application No. WO2013/155262
Patent Document 3: International Patent Application No. WO2013/151938

Non-Patent Documents

Non-patent Document 1: Int. Urogynecol. J., 14(6), 367-372 (2003)
Non-patent Document 2: Am. J. Physiol. Renal. Physiol., 292(2), 639-646 (2007)
Non-patent Document 3: J. Urol., 181(6), 2628-2633 (2009)
Non-patent Document 4: American Urological Association poster 1667 (2008)
Non-patent Document 5: Urology, 62(4 Suppl. 1), 31-38 (2003)
Non-patent Document 6: Nat. Med., 18(3), 452-455 (2012)
Non-patent Document 7: Acta Neuropathol., 60(3-4), 278-282 (1983)
Non-patent Document 8: Neurourol. Urodyn., 17(3), 197-205 (1998)

OUTLINE OF THE INVENTION

Problems that the Invention is to Solve

The problem that the invention is to solve is to provide a novel pharmaceutical composition for prevention and/or treatment of urinary incontinence, in a certain aspect, a pharmaceutical composition for prevention and/or treatment of stress urinary incontinence, and in a certain aspect, a pharmaceutical composition for prevention and/or treatment of mixed urinary incontinence, which differ from conventional drugs.

Means of Solving the Problems

As a result of extensive studies to solve the problems, the present inventors discovered that a pharmaceutical composition comprising 1-[2-({[trans-3-fluoro-1-(3-fluoropyridin-2-yl)cyclobutyl]methyl}amino)pyrimidin-5-yl]-1H-pyrrole-3-carboxamide or a salt thereof, as an active ingredient is useful for prevention and/or treatment of urinary incontinence, and so perfected the present invention.

Specifically, the present invention relates to a pharmaceutical composition for prevention and/or treatment of urinary incontinence, in a certain aspect, a pharmaceutical composition for prevention and/or treatment of stress urinary incontinence, and in a certain aspect, a pharmaceutical composition for prevention and/or treatment of mixed urinary incontinence, containing 1-[2-({[trans-3-fluoro-1-(3-fluoropyridin-2-yl)cyclobutyl]methyl}amino)pyrimidin-5-yl]-1H-pyrrole-3-carboxamide or a salt thereof, and a pharmaceutically acceptable excipient or a salt thereof.

The present invention also relates to a therapeutic agent for prevention and/or treatment of urinary incontinence, in a certain aspect, a therapeutic agent for prevention and/or treatment of stress urinary incontinence, and in a certain aspect, a therapeutic agent for prevention and/or treatment of mixed urinary incontinence, containing 1-[2-({[trans-3-fluoro-1-(3-fluoropyridin-2-yl)cyclobutyl]methyl}amino) pyrimidin-5-yl]-1H-pyrrole-3-carboxamide or a salt thereof.

The present invention also relates to a therapeutic agent for prevention and/or treatment of urinary incontinence, in a certain aspect, a therapeutic agent for prevention and/or treatment of stress urinary incontinence, and in a certain aspect, a therapeutic agent for prevention and/or treatment of mixed urinary incontinence, containing 1-[2-({[trans-3-fluoro-1-(3-fluoropyridin-2-yl)cyclobutyl]methyl}amino) pyrimidin-5-yl]-1H-pyrrole-3-carboxamide or a salt thereof, and a pharmaceutically acceptable excipient.

The present invention also relates to use of 1-[2-({[trans-3-fluoro-1-(3-fluoropyridin-2-yl)cyclobutyl]methyl}amino) pyrimidin-5-yl]-1H-pyrrole-3-carboxamide or a salt thereof to manufacture a pharmaceutical composition for prevention and/or treatment of urinary incontinence, in a certain aspect, a pharmaceutical composition for prevention and/or treatment of stress urinary incontinence, and in a certain aspect, a pharmaceutical composition for prevention and/or treatment of mixed urinary incontinence; use of 1-[2-({[trans-3-fluoro-1-(3-fluoropyridin-2-yl)cyclobutyl]methyl}amino) pyrimidin-5-yl]-1H-pyrrole-3-carboxamide or a salt thereof for prevention and/or treatment of urinary incontinence, in a certain aspect, for prevention and/or treatment of stress urinary incontinence, and in a certain aspect, for prevention and/or treatment of mixed urinary incontinence; 1-[2-({[trans-3-fluoro-1-(3-fluoropyridin-2-yl)cyclobutyl] methyl}amino)pyrimidin-5-yl]-1H-pyrrole-3-carboxamide or a salt thereof for prevention and/or treatment of urinary incontinence, in a certain aspect, for prevention and/or treatment of stress urinary incontinence, and in a certain aspect, for prevention and/or treatment of mixed urinary incontinence; and a therapeutic method for prevention and/or treatment of urinary incontinence, in a certain aspect, a therapeutic method for prevention and/or treatment of stress urinary incontinence, and in a certain aspect, a therapeutic method for prevention and/or treatment of mixed urinary incontinence, comprising or consisting of administering an effective dose to a subject of 1-[2-({[trans-3-fluoro-1-(3-fluoropyridin-2-yl)cyclobutyl]methyl}amino)pyrimidin-5-yl]-1H-pyrrole-3-carboxamide or a salt thereof. "Subject" refers to a human or other animal requiring prevention and/or treatment of urinary incontinence, and in certain aspects, to a human requiring prevention and/or treatment of urinary incontinence.

Effects of the Invention

Compound A or a salt thereof, which is the active ingredient of the pharmaceutical composition of the present invention, is expected as the active ingredient of a pharmaceutical composition for prevention and/or treatment of urinary incontinence, in a certain aspect, a pharmaceutical composition for prevention and/or treatment of stress urinary incontinence, and in a certain aspect, a pharmaceutical composition for prevention and/or treatment of mixed urinary incontinence because Compound A reinforced contractile response of the external urethral sphincter induced by transmural electrical stimulation of an extracted rat urethra and reinforced a reaction increasing urethra internal pressure by electrical stimulation of a rat pudendal nerve.

This description includes the contents of the description, claims and drawings of Japanese Patent Application No. 2014-183434, which is a priority document of the present application.

EMBODIMENT OF THE INVENTION

Figure 1:
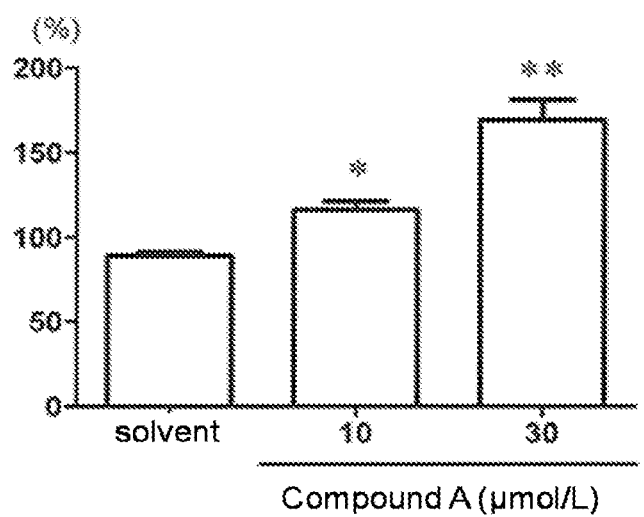
FIG. 1 is a graph showing results of Example 1. The vertical axis shows the percentage (%) (average ± standard error) of contractile response of an external urethral sphincter induced by transmural electrical stimulation of an extracted rat urethra after adding a test substance to before adding the test substance. * indicates that a significant difference from a solvent-added group was found when tested for a statistical level of less than 5% using Dunnett's multiple comparison procedure ($p<0.05$), and ** indicates that a significant difference from the solvent-added group was found when tested for a statistical level of less than 1% using the same procedure ($p<0.01$).

The present invention will described in detail hereinafter.

As described earlier, Compound A has the chemical name of 1-[2-({[trans-3-fluoro-1-(3-fluoropyridin-2-yl)cyclobutyl]methyl}amino)pyrimidin-5-yl]-1H-pyrrole-3-carboxamide, and is the chemical described in Example 14 of Patent Document 1 cited earlier. The chemical structure of Compound A is as follows.

CHEMICAL EXPRESSION 1

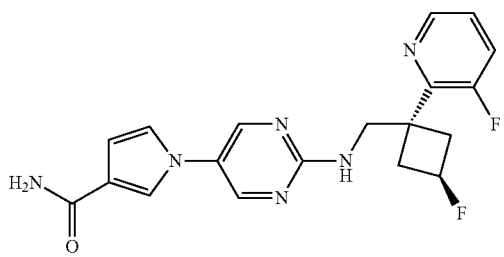

In the present specification, "urinary incontinence" is a condition in which urine leaks involuntarily; examples of which include stress urinary incontinence, urge urinary incontinence, mixed urinary incontinence, functional urinary incontinence, and reflex urinary incontinence.

"Stress urinary incontinence" is a condition in which urine leaks involuntarily, regardless of contraction of the bladder, with elevated abdominal pressure associated with coughing, sneezing, movement, or the like, and "urge urinary incontinence" is a condition in which urine leaks involuntarily following a sudden, irresistible strong urge to urinate (urinary urgency). "Mixed urinary incontinence" is a condition in which both stress urinary incontinence and urge urinary incontinence occur.

The application of the pharmaceutical composition of the present invention is for urinary incontinence, in a certain aspect, for stress urinary incontinence or mixed urinary incontinence, in a certain aspect, for stress urinary incontinence, and in a certain aspect, for mixed urinary incontinence. The application of the pharmaceutical composition of the present invention is for diseases which can be prevented or treated by reinforced contraction of the external urethral sphincter.

The present invention has the following modes.

(1) A pharmaceutical composition for prevention and/or treatment of urinary incontinence containing Compound A and a pharmaceutically acceptable excipient. In a certain aspect, a pharmaceutical composition for prevention and/or treatment of stress urinary incontinence containing Compound A and a pharmaceutically acceptable excipient. In a certain aspect, a pharmaceutical composition for prevention and/or treatment of mixed urinary incontinence containing Compound A and a pharmaceutically acceptable excipient.

(2) An agent for prevention and/or treatment of urinary incontinence containing Compound A. In a certain aspect, an agent for prevention and/or treatment of stress urinary incontinence containing Compound A. In a certain aspect, an agent for prevention and/or treatment of mixed urinary incontinence containing Compound A.

(3) Use of Compound A for manufacturing a pharmaceutical composition for prevention and/or treatment of urinary incontinence. In a certain aspect, use of Compound A for manufacturing a pharmaceutical composition for prevention and/or treatment of stress urinary incontinence. In a certain aspect, use of Compound A for manufacturing a pharmaceutical composition for prevention and/or treatment of mixed urinary incontinence.

(4) Use of Compound A for prevention and/or treatment of urinary incontinence. In a certain aspect, use of Compound A for prevention and/or treatment of stress urinary incontinence. In a certain aspect, use of Compound A for prevention and/or treatment of mixed urinary incontinence.

(5) Compound A for prevention and/or treatment of urinary incontinence. In a certain aspect, Compound A for prevention and/or treatment of stress urinary incontinence In a certain aspect, Compound A for prevention and/or treatment of mixed urinary incontinence.

(6) A therapeutic method for prevention and/or treatment of urinary incontinence, comprising or consisting of administering an effective dose of Compound A to a subject. In a certain aspect, a therapeutic method for prevention and/or treatment of stress urinary incontinence, comprising or consisting of administering an effective dose of Compound A to a subject. In a certain aspect, a therapeutic method for prevention and/or treatment of mixed urinary incontinence, comprising or consisting of administering an effective dose of Compound A to a subject.

Compound A or a salt thereof may be acquired following the method described in Example 14 of the Patent Document 1 cited earlier (International Patent Application No. WO2011/133888), or by a modification of this method.

A "salt of Compound A" refers to a pharmaceutically acceptable acid addition salt of Compound A; specifically, an acid addition salt with an inorganic salt such as hydrochloric acid, hydrobromic acid, sulfuric acid, nitric acid, or phosphoric acid, or an organic salt such as acetic acid, propionic acid, glycolic acid, pyruvic acid, malic acid, oxalic acid, malonic acid, succinic acid, malonic acid, maleic acid, lactic acid, benzoic acid, cinnamic acid, mandelic acid, tartaric acid, ascorbic acid, methanesulfonic acid, ethanesulfonic acid, p-toluenesulfonic acid, 2-hydroxyethanesulfonic acid, stearic acid, or salicylic acid. "Compound A or a salt thereof" includes solvates of Compound A, specifically, for example, a hydrate or ethanolate; and acid addition salts of solvates of Compound A.

One mode of "Compound A or a salt thereof" is Compound A.

A pharmaceutical composition containing Compound A or a salt thereof may be prepared by a method used conventionally, using an excipient conventionally used in the art; that is, a drug excipient, a drug carrier, or the like.

The composition may be administered by oral dosing using a tablet, a pill, a capsule, granules, a powder, a liquid, or the like, or by any non-oral mode, such as an intraarticular, intravesicular, intravenous, intramuscular, or other injection, a suppository, a transdermal solution, an ointment, a transdermal patch, a transmucosal solution, a transmucosal patch, or an inhalant.

A tablet, a powder, granules, or the like is used as a solid composition for oral dosing. One or more active ingredients in such a solid composition is mixed with at least one inert excipient. The composition may contain inert additives, such as a lubricant or disintegrator, a stabilizer, or a solubilizer, following a conventional method. A tablet or a capsule may be coated as required with a sugar coating or a film of a gastro-enteric or enteric material.

A liquid composition for oral dosing contains a pharmaceutically acceptable emulsion, solution, suspension, syrup, elixir, or the like, and contains a conventionally used diluent such as purified water or ethanol. The liquid composition may also contain a solubilizer other than the inert diluent, a moisturizer, an adjuvant such as a suspension, a sweetener, a flavoring, a fragrance, or a preservative.

An injection for non-oral administration contains a sterile aqueous or nonaqueous solvent, suspension, or emulsion. Aqueous solvents include, for example, distilled water for injection or physiological saline. Nonaqueous solvents include, for example, alcohols such as ethanol. Such a composition may also contain a tonicity agent, a preservative, a moisturizer, an emulsifier, a dispersant, a stabilizer, or a solubilizer. The composition is sterilized, for example, by filtering through a bacteria-retaining filter or by irradiating. The composition may also be manufactured as a sterile solid composition, and dissolved or suspended in sterile water or a sterile injection solvent before use.

In the case of standard oral dosing, a suitable daily dose is about 0.001-100 mg/kg, preferably 0.01-30 mg/kg, and more preferably 0.1-10 mg/kg per body weight, given once or divided and given 2-4 times. In the case of intravenous dosing, 0.0001-10 mg/kg per body weight, is given once daily or divided and given several times daily. As a transmucosal agent, about 0.001-100 mg/kg per body weight is given. The dose may be suitably determined according to individual conditions considering the symptoms, age, and sex of the subject.

Although this will differ depending on the route of administration, the dosage form, the administration site, and the type of excipient and additives, the pharmaceutical composition of the present invention contains 0.01-99 wt %, and in certain modes, 0.01-50 wt % of Compound A or a salt thereof as an active ingredient.

The pharmaceutical composition of the present invention may be used in combination with various types of therapeutic agents considered to be effective on urinary incontinence, especially stress urinary incontinence or mixed urinary incontinence. The therapeutic agent may be administered simultaneously, separately afterward, or after an arbitrary time gap. If administered simultaneously, the therapeutic agent may be formulated together with or separately from the pharmaceutical composition.

EXAMPLES

The pharmacological effects of the pharmaceutical composition of the present invention were confirmed by the following examples.

Example 1

Test to Evaluate Reinforcing Action of Compound A on External Urethral Sphincter Contractile Response Induced by Transmural Electrical Stimulation Using Extracted Rat Urethra Experimental Method The urethra was extracted from a 10-week-old SD female rat (Japan SLC, Inc.). The extracted urethra was cut open vertically, then sliced into specimen strips having a width of about 3 mm, which were dangled in a circular direction in 10-mL tissue buses filled with Krebs-Henseleit buffer. The Krebs-Henseleit buffer was aerated with 95% $O_2$ and 5% $CO_2$, and kept warm at 37° C. Resting tension was set to about 0.5 g, and isometric contraction was recorded using a tension transducer (TB-611T; Nihon Kohden), an amplifier (AP-621G; Nihon Kohden), and an interface (PowerLab 8/30; AD Instruments). After resting tension had stabilized, contractile response (mg) of the external urethral sphincter was confirmed by transmural electrical stimulation (stimulation voltage: 20 V, pulse width: 30 μsec, stimulation frequency: 0.2 Hz, stimulation time: 15 sec). After contractile response of the external urethral sphincter was provoked three times at 30-second intervals by transmural electrical stimulation (stimulation voltage: 20 V, pulse width: 30 μsec, stimulation frequency: 20 Hz, stimulation time: 1 sec) in the absence of the test substance, a solvent (dimethylsulfoxide: DMSO) or Compound A dissolved in DMSO to final concentrations of 10 or 30 μmol/L were added to the tissue buses, and contractile response was provoked three times at 30-second intervals 15 minutes later by transmural electrical stimulation under the same conditions. The average of contractile response by electrical stimulation three times each before and after adding the test substance was calculated, and the percentage of the contractile response after adding the test substance to the contractile response before adding the test substance was calculated for each concentration group. After performing the test for n=6 in each group, the Compound A-added groups were compared with the solvent-added group by Dunnett's multiple comparison procedure, and seen as significantly different when p<0.05.

Effect

As shown in FIG. 1, Compound A reinforced contractile response of the external urethral sphincter induced by transmural electrical stimulation of an extracted rat urethra.

Example 2

Test to Evaluate Reinforcing Action of Compound A on Reaction Increasing Urethra Internal Pressure Induced by Electrical Stimulation of Rat Pudendal Nerve Experimental Method SD female rats (Japan SLC, Inc.) having a body weight of 200-350 g were anesthetized with urethane (1.2 g/kg, sc; Sigma-Aldrich), and a catheter (PE-50; Becton Dickinson) was lodged in the jugular vein for administering the test substance. Laparotomies were performed, and the dome of the bladder was cut open to allow discharge of the urine in the bladder. A microchip pressure transducer catheter (3.5Fr; Millar Instruments) was inserted from the external urethral orifice toward the bladder to measure the urethra internal pressure. The rats were arranged prone, the back was cut open, and several left and right pudendal nerves were isolated and held in place with exciting electrodes. The microchip pressure transducer catheter was linked to an amplifier (AP-601G; Nihon Kohden) and an interface (PowerLab 8/30; AD Instruments), and the part of the pressure transducer inside the urethra was fixed in a location near the site having the greatest urethra internal pressure (about 10-15 mm from the urethral orifice) while measuring the urethra internal pressure. The pudendal nerves were electrically stimulated (stimulation voltage: maximum of 10 V, pulse width: 50 μsec, stimulation frequency: 20 Hz, stimulation time: 400 msec) every one minute, and after a stabilized reaction increasing urethra internal pressure (mmHg) was confirmed, a solvent (13.3% DMSO, 13.3% polyethylene glycol 400, 13.3% Tween 20, and 60% distilled water) or Compound A dissolved in the solvent at 1 mL/kg were intravenously administered to final doses of 3 or 10 mg/kg. The average of the reactions increasing urethra internal pressure by electrical stimulation three times before administering the test substance was calculated as the level before administering the test substance, and the percentage of reaction increasing urethra internal pressure by electrical stimulation about three minutes after administering the test substance to the value before administering the test substance was calculated for each of the treatment groups. After performing the test for n=6 in each group, the Compound A groups were compared with the solvent group by Dunnett's multiple comparison procedure, and seen as significantly different when p<0.0.5.

Effect

Figure 2:
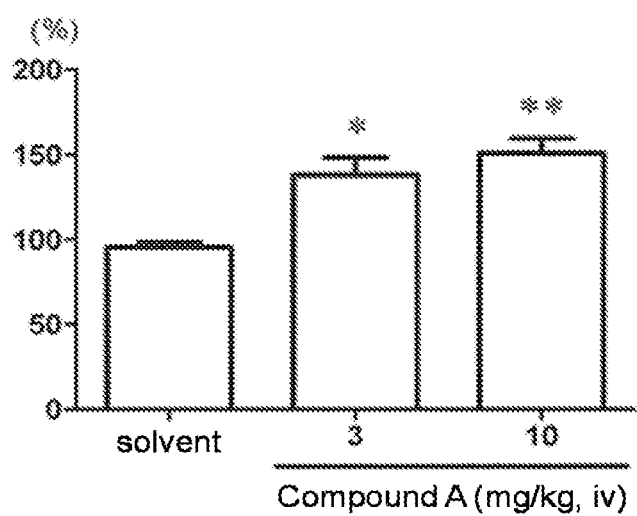
FIG. 2 is a graph showing results of Example 2. The vertical axis shows the percentage (%) (average ± standard error) of reaction increasing urethra internal pressure induced by electrical stimulation of the rat pudendal nerve after administering a test substance to before administering the test substance. * indicates that a significant difference from a solvent-added group was found when tested for a statistical level of less than 1% using Dunnett's multiple comparison procedure ($p<0.01$), and ** indicates that a significant difference from a solvent-added group was found when tested for a statistical level of less than 0.1% using Dunnett's multiple comparison procedure ($p<0.001$).

As shown in FIG. 2, Compound A reinforced a reaction increasing urethra internal pressure by electrical stimulation of the rat pudendal nerve.

As described earlier, Compound A clearly increases urethra internal pressure by reinforcing the contractile force of the external urethral sphincter dependent on stimulus of the dominant nerve of the external urethral sphincter, suggesting that urinary incontinence may be controlled by increasing urethral resistance. Therefore, Compound A having fast muscle troponin activation is expected as a therapeutic agent and/or a prophylactic for urinary incontinence, especially stress urinary incontinence or mixed urinary incontinence.

INDUSTRIAL APPLICABILITY

Compound A or a salt thereof, which is the active ingredient of the pharmaceutical composition of the present invention, is expected as the active ingredient of a pharmaceutical composition for prevention and/or treatment of urinary incontinence, in a certain aspect, a pharmaceutical composition for prevention and/or treatment of stress urinary incontinence, and in a certain aspect, a pharmaceutical composition for prevention and/or treatment of mixed urinary incontinence.

All publications, patents, and patent applications cited herein are incorporated herein by reference in their entirety.

The invention claimed is:

1. A method for treatment of urinary incontinence, comprising administering an effective dose of 1-[2-({[trans-3-fluoro-1-(3-fluoropyridin-2-yl)cyclobutyl]methyl}amino)pyrimidin-5-yl]-1H-pyrrole-3-carboxamide or a salt thereof to a subject in need thereof.

2. A method according to claim 1, wherein said urinary incontinence is stress urinary incontinence.

3. A method according to claim 1, wherein said urinary incontinence is mixed urinary incontinence.

* * * * *